United States Patent [19]

Eibofner

[11] 4,047,301
[45] Sept. 13, 1977

[54] DENTAL HANDPIECE

[75] Inventor: Eugen Eibofner, Biberach, Germany

[73] Assignee: Kaltenbach & Voigt, Biberach an der Riss, Germany

[21] Appl. No.: 684,453

[22] Filed: May 7, 1976

[30] Foreign Application Priority Data

May 13, 1975 Germany .............................. 2521313

[51] Int. Cl.² .............................................. A61C 1/10
[52] U.S. Cl. ....................................................... 32/27
[58] Field of Search .................. 64/21; 32/26, 27; 415/403, 12

[56] References Cited

U.S. PATENT DOCUMENTS 3,411,212   11/1968   Staunt ...................................... 32/27
3,656,318   4/1972   Smith ........................................ 64/21

Primary Examiner—Robert Peshock

[57] ABSTRACT

A dental handpiece comprises a holding sleeve, a head sleeve connected to the holding sleeve for mounting a dental instrument, a connecting zone providing an interconnection between the holding sleeve and the head sleeve, a two-part drive shaft housed within the handpiece, a first part of the shaft being arranged within the holding sleeve and a second part of the shaft being arranged within the head sleeve, and a ball-type planetary transmission housed within the connecting zone and providing a drive connection between the first and second parts of the shaft. The handpiece may be a straight handpiece or the head sleeve may be inclined to the holding sleeve to provide an angled handpiece.

10 Claims, 7 Drawing Figures

DENTAL HANDPIECE

This invention relates to a dental handpiece comprising a holding sleeve, a head sleeve connected to said holding sleeve and adapted to mount rotatably a dental instrument, a connecting zone providing an interconnection between said holding sleeve and said head sleeve, a two-part shaft housed within the handpiece, a first part of the shaft being arranged within the holding sleeve and a second part of the shaft being arranged within the head sleeve, and a transmission housed within said connecting zone and providing a drive connection between said first and second part of the shaft.

The invention is particularly, though not exclusively, concerned with a dental handpiece of the above type, in which the head sleeve has its longitudinal axis inclined relative to the longitudinal axis of the holding sleeve.

A dental handpiece is known from German specification No. 1,219,170 in which the zone of the bend connection or location between the holding and head sleeve provides sufficient space for the transmission or gearing disposed therein and which comprises driving pinions provided at the ends facing each other of the two drive shaft parts or elements. The manufacture of such gearing is, however, costly since the driving pinions must by synchronised with each other. Additionally, there is a limit to the gearing-down or gearing-up ratio achievable by means of the gearing, since the gearwheels of relatively large diameter which would be required for this purpose cannot be used due to the fact that it is necessary to keep the dimensions of dental handpieces relatively small.

According to one aspect the invention provides a dental handpiece comprising a holding sleeve;
- a head sleeve connected to said holding sleeve and adapted to mount rotatably a dental instrument, said head sleeve having its longitudinal axis inclined relative to the longitudinal axis of the holding sleeve;
- a connecting zone providing an interconnection between said holding sleeve and said head sleeve;
- a two-part drive shaft housed within the hand piece, a first part of the shaft being arranged within the holding sleeve and a second part of the shaft being arranged within the head sleeve;
- and a transmission providing a drive connection between said first and second parts of the shaft, said transmission being housed within said connecting zone;

wherein the transmission comprises a ball-type planetary transmission.

Thus, according to an embodiment of the invention, a transmission is provided which is simple to manufacture and which makes possible, without substantial enlargement of the diameter of the handpiece (sleeve) the achievement of relatively considerable gearing-down or gearing-up ratios.

It is preferred that the ball-type planetary transmission comprises an inner ring, an outer ring, balls frictionally engageable between said rings, and a cage engaging said balls. One of the parts of the shaft is coupled with the cage, and one of the rings is arranged to be non-rotatable and the other ring is arranged to be rotatable on the other part of the shaft, with the latter. Even a slight variation of the diameter of the balls of the transmission results in an effective variation of the stepping-down or stepping-up ratio, so that variation or enlargement of the handpiece diameter is unnecessary. The latter is in particular unnecessary if, for example, for achievement of a larger stepping-up ratio the ball diameter is enlarged and for example the diameter of the inner ring, contacting the balls, of the (driven) second part of the shaft mounted in the head sleeve is reduced. Manufacture of the ball-type planetary transmission is found to be relatively simple, since the high degree of dimensional accuracy and adaptation of the gearing elements required in the case of the teeth of driving pinions in the known arrangement is unnecessary.

Dental handpieces having stepping-down ball-type planetary transmission or gearing are known per. se from German specification No. 1,055,752 and German utility model No. 6,913,202. However, what is concerned in that case is straight handpieces. In fact, they do not have the head sleeve bent-over through an obtuse angle relative to the holding sleeve, or the transverse division, provided in the zone of the bending location, of the drive shaft mounted in the handpiece. In the case of the handpiece according to one aspect of the invention, there is afforded at the bending location, for constructional reasons, sufficient space for accommodating gearing. In the case of straight handpieces, on the other hand, the gearing involves enlargement of the diameter of the dental handpiece in the zone of the gearing. In the case of the known, straight handpieces, this enlarged zone is precisely at that location at which the dentist holds the handpiece during treatment, and this is uncomfortable and inconvenient for the dentist. If, furthermore, the known arrangement of a ball and planet gearing employed in straight handpieces should be transferred to handpieces having a bent-over or "kinked" head sleeve, then it would be necessary to introduce into the drive shaft rearwardly of the transmission, in the zone of the bending location, supplementary gearing for deflecting the drive force of the drive shaft into the head piece.

In the case of the dental turbine handpiece disclosed in German specification No. 1,055,752, one of the drive shaft parts or elements engages cage-like with the balls of the ball and planet gearing the balls of which are mounted, with frictional engagement, between an inner ring and an outer ring, one of the said rings being arranged to be non-rotatable and the other ring being arranged to be rotatable on the other drive shaft element, with the latter, and one of the said rings being axially displaceable under the action of a displacement ring for the purposes of adjusting or engaging the balls. Associated with the displacement ring axially displaceable in the case of this known handpiece of a leaf spring which is fast at one of its ends, outwardly curved, extends in the longitudinal direction of the handpiece and, under increased loading of the instrument driven by the drive shaft and, therewith, required increased torque, must be manually compressed so that there takes place elongation or stretching of the leaf spring which then presses at its non-fixed end against the displacement ring, whereby the latter is, whilst overcoming the force of a helical spring, displaced towards the axially displaceable but non-rotatably arranged outer ring of the ball and planet gearing and displaces the said outer ring for the purpose of adjusting the ball and therewith for the purpose of increasing the transmitted torque. Manual actuation of the leaf spring is inconvenient and a burden to the dentist, especially since, apart from monitoring the dental treatment process proper he is also required to pay attention to adjustment suitable for correct torque transmission of the balls of the ball and planet gearing.

According to a further aspect of the invention there is provided a dental handpiece comprising a holding sleeve;
- a head sleeve connected to said holding sleeve and adapted rotatably to mount a dental instrument;
- a connecting zone providing an interconnection between said holding sleeve and said head sleeve;
- a two-part drive shaft housed within the handpiece, a first part of the shaft being arranged within the holding sleeve and a second part of the shaft being arranged within the head sleeve;
- and a ball-type planetary transmission housed within the said connecting zone and providing a drive connection between said first and second parts, the ball-type planetary transmission comprising an inner ring, an outer ring, balls frictionally engageable between said rings, and a cage engaging said balls;
- wherein one of said parts of the drive shaft is coupled drivingly with said cage;
- one of said rings is non-rotatably mounted in said connecting zone;
- a coupling element is secured to the other of said parts of the shaft;
- and the other of said rings is coupled with said other part of the shaft for rotation therewith, said other ring having a drive transmitting connection with said coupling element and being axially displaceable relative to said other part of the shaft in order to adjust the frictional engagement of said balls between said inner and outer rings thereby to alter the value of torque transmissible by the shaft;
- and wherein said drive transmitting connection comprises interengaging helical teeth provided on said coupling element and on said other ring.

The handpiece according to the further aspect of the invention may be a straight handpiece or an angled handpiece having the head sleeve inclined to the holding sleeve.

On loading the instrument driven by the drive shaft in use, there occurs braking of the driven shaft part mounted in the head sleeve coaxial with the holding sleeve or bent-over relative thereto, so that relative rotation of this shaft part relative to the other (i.e. the driving shaft part) takes place. This relative rotation of the two drive shaft parts produces the effect that the tooth profiles of the two intermeshing helical toothings slide against each other in such manner that the axially displaceable inner ring of outer ring travels away in the axial direction from the shaft part having the coupling element secured thereto and which is axially non-displaceable, i.e. is displaced away from the coupling element. Thereby, automatic adjustment, and therewith increase of the application pressure of the balls of the transmission, in the event of increased loading of the shaft part mounted in the head sleeve, is achieved.

Annular grooves may be provided for mounting the balls on the peripheral faces facing each other of the inner ring and the outer ring, and serve, after termination of the increased loading to bring about return of the balls into the normal position and therewith, automatically also termination of the adjustment.

A concavely curved design may be provided for the toothed profiles, in particular in respect of one of the two helical toothings, so as to produce the result that due to the "slidingup," taking place at the curved tooth profiles, of the teeth of the other helical toothing, the desired increased torque transmission is very rapidly initiated.

Expediently, the coupling element is arranged on the shaft part mounted in the head sleeve.

In one preferred embodiment the inner ring is axially displaceable on the shaft part mounted in the head sleeve and, due to the mutual engagement of the oblique toothings, is arranged to be rotatable with the shaft part, the driving shaft part mounted in the holding sleeve engaging with the balls of the transmission via the cage.

In order to reliably prevent tilting or jamming of the coupling element with the axially displaceable inner ring or outer ring, it is proposed to arrange the teeth of the helical toothings to be uniformly distributed about the periphery of the coupling element and of the axially displaceable inner ring or outer ring.

It is expedient if the inner ring or the outer ring is connected to be fast with a sleeve directed towards the coupling element and on which is provided the helical toothing, and which is arranged to be axially displaceable and rotatable on the associated shaft part.

DESCRIPTION OF THE PREFERRED EMBODIMENTS

Figure 1:
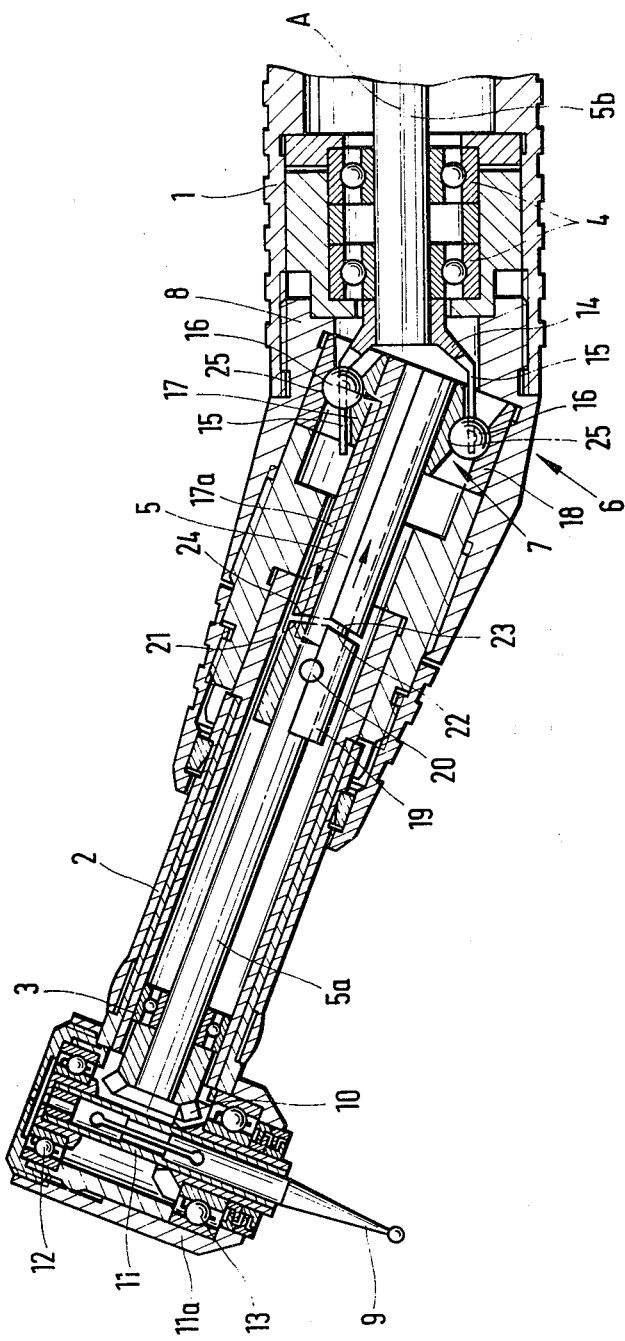
FIG. 1 is a longitudinal sectional view of one embodiment of dental handpiece according to the invention.

The dental handpiece shown in FIG. 1 comprises a holding sleeve 1 (for the user) and a head sleeve 2 connected to sleeve 1 and inclined relative to the longitudinal axis A of the sleeve 1. A two-part drive shaft 5 is mounted in the handpiece with the aid of bearings 3, 4, and is transversely divided in the zone of a bending location 6 between sleeves 1 and 2. The two drive shaft elements 5a and 5b thus formed are drivingly interconnected by a ball-type planetary transmission 7 housed within the connecting zone (6). The holding sleeve 1 and the head sleeve 2 constitute two independent elements releasably connected with each other by a screw thread 8.

The drive shaft element 5a is the driven element and is mounted in the head sleeve 2 for rotation by the (driving) drive shaft element 5b via the transmission 7, for driving a dental instrument 9 coupled therewith, for example a drill. For this purpose, the drive shaft element 5a engages, via a toothed-wheel or bevel gear 10, with a drive sleeve 11 holding the instrument 9 and arranged at right angles to the drive shaft element 5a, bearings 12 and 13 for the drive sleeve 11 being arranged in an angle head 11a.

Figure 4:
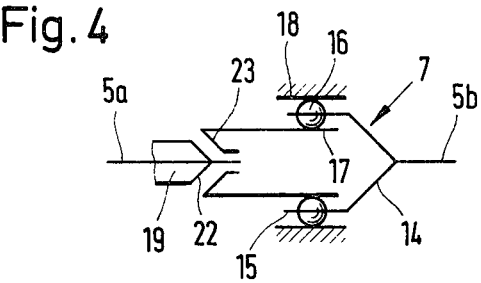
FIGS. 4 to 7 are diagrammatic illustrations of different constructions of ball-type planetary transmission for use in the handpiece.
Figure 5:
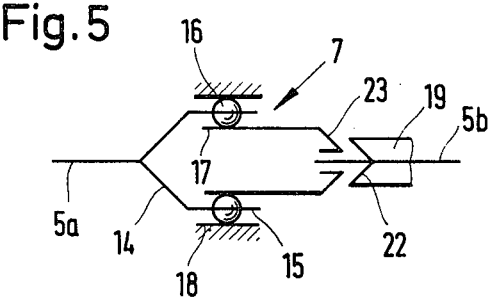

The transmission 7 may be designed in different ways, as shown diagrammatically in FIGS. 4 to 7. The illustration of transmission according to FIG. 4 corresponds, in its structure, to the embodiment according to FIG. 1, wherein step-up transmission takes place in the ratio 1 : 2.7 from the driving shaft element 5b to the driven shaft element 5a whereas FIG. 5 shows an embodiment of stepping-down transmission.

Figure 2:
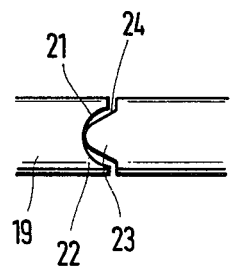
FIG. 2 is a detail cross-sectional view illustrating a ball-type planetary transmission for coupling together two parts of a drive shaft provided in the handpiece in FIG. 1.

In each case, a cage-like end 14 facing the transmission 7 of one of the drive shaft elements (5b in FIGS. 1, 4 and 7 or 5a in FIGS. 5 and 6) is designed in the manner of a cage open at its end facing the other drive shaft element, in the form of a round fork. Through the agency of webs 15 of the cage, the end 14 engages between the balls 16 of the ball-type planetary transmission 7 (cf. also FIG. 2, showing the transmission 7 in cross section). The balls 16 are mounted, with frictional engagement, between an inner ring 17 and an outer ring 18. One of the rings 17, 18 is non-rotatably arranged, (outer ring 18 in FIGS. 1, 4 and 5 and inner ring 17 in FIGS. 6 and 7). The other ring (in FIGS. 1, 4 and 5 the inner ring 17 and in FIGS. 6 and 7 the outer ring 18) is mounted for rotation on and with a respective drive shaft element. Thus, inner ring 17 is rotatable respectively with shaft element 5a in FIGS. 1 and 4, and shaft element 5b in FIG. 5, whereas outer ring 18 is rotatable respectively on shaft element 5b in FIG. 6 and 5a in FIG. 7.

Figure 6:
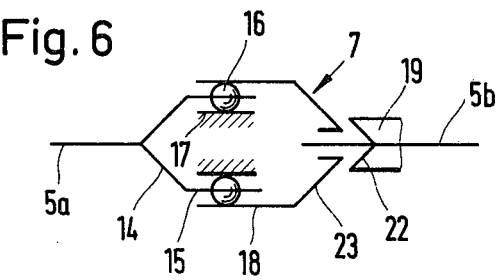
Figure 7:
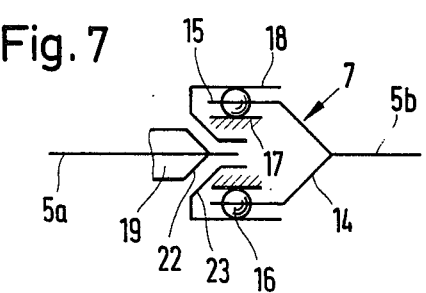

One of the rings 17, 18, i.e. in each particular instance the ring rotatable with the drive shaft element 5a in FIGS. 1, 4 and 7, or with shaft element 5b in FIGS. 5 and 6, not engaging with a balls 16, i.e. in FIGS. 1, 4 and 5 the inner ring 17 and in FIGS. 6 and 7 the outer ring 18, is axially displaceable and rotatable under the influence of a coupling element in the form of displacement ring 19. The ring 19 is shown only diagrammatically in FIGS. 4 to 7, but is shown in detail in FIG. 1 in which it is held fast by means of a transverse pin 20 on the drive shaft element 5a. This applies also to FIGS. 1, 4 and 7, but in FIGS. 5 and 6 the ring 19 will be secured to shaft element 5b by pin 20.

Figure 3:
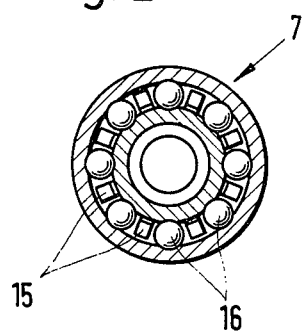
FIG. 3 is a detail view of a part of the transmission provided in the handpiece.

For this purpose, the displacement ring 19 according to FIGS. 1 and 3 is provided with helical gear teeth 22 having straight and/or curved tooth profiles 21 and meshing with corresponding helical toothing 23 provided on the associated axially displaceable ring (inner ring 17 in FIGS. 1, 4 and 5 or outer ring 18 in FIGS. 6 and 7). In the case of the helical toothings 22, 23, the cone angle is larger than the friction angle.

During normal operation of the instrument 9, the helical toothings 22, 23 serve substantially only for transmitting rotational movement between the axially displaceable ring 17 and the displacement ring 19, and therewith the drive shaft element 5a in FIGS. 1, 4 and 7 or shaft element 5b in FIGS. 5 and 6.

During idle travel, the balls 16 are driven by the cage webs 15. Due to the centrifugal force of the balls 16, the latter are pressed against the outer ring 18. The movement, reciprocating relative to the balls 16, of the cage webs 15 presses the balls in the direction of the ends of the webs; thus, the webs 15 endeavour to press the balls 16 out between the inner ring 17 and the outer ring 18. Thereby, also in cooperation with annular grooves 25 formed in the inner ring 17 and the outer ring 18 (See FIG. 1), frictional engagement is produced so that the inner ring 17 is driven. Via the tooth profiles 21, 24 of the helical toothings 22,23, the drive shaft element 5a is set in rotation. The friction in the bearings, 3, 12 and 13 produces the result that the drive shaft element 5a rotates relative to the drive shaft element 5b and thereby, via the profiles 21, 24, the inner ring 17 is pressed only slightly axially but adequately for rotation transmission against the balls. Therewith, transmission of rotation is guaranteed.

When the instrument 9 is loaded, in that its rotation is prevented or retarded for example at a tooth to be treated, the relative rotation thereby occurring of the two drive shaft elements 5a and 5b, and therewith of the displacement ring 19 and of the inner ring 17 in FIGS. 1, 4 and 5 or the outer 18 in FIGS. 6 and 7, produces the result that the tooth profiles 21, 24 of the two helical gearings 22, 23 slide against each other in the sense of a displacement, taking place in the axial direction, of the inner ring 17 in FIGS. 1, 4 and 5 or of the outer ring 18 in FIGS. 6 and 7, so that automatic adjustment takes place of the balls 16 mounted in the annular grooves 25 of the inner ring 17 and of the outer ring 18 so as to increase the transmission of torque between the shaft elements 5a and 5b.

The teeth of the helical gearings 22, 23 are uniformly distributed over the periphery of the displacement ring 19 and the inner ring 17 in FIG. 1, 4 and 5 or the outer ring 18 in FIG. 6 and 7, and are so designed that no automatic locking can occur.

In the case of the embodiments according to FIGS. 1, 4 and 7, the displacement (caused by the rotation of the displacement ring 19) of the inner ring 17 in FIGS. 1 and 4 or of the outer ring 18 in FIG. 7 takes place relative to the driven shaft element 5a which consequently directly influences the loading of the instrument 9, whereas in the case of the embodiments according to FIGS. 5 and 6 this occurs at the driving shaft element 5b.

In the case of the embodiments according to FIGS. 4 to 7, the drive shaft elements 5a and 5b are shown coaxial as for application to straight (non-angled) handpieces; however, they could, as in the case of the embodiment according to FIG. 1, be inclined at an obtuse angle relative to each other for use with handpieces having a head sleeve (2) inclined relative to the holding sleeve (1).

Referring to FIG. 1, the inner ring 17 is fast with a sleeve 17a extending towards the displacement ring 19 and at which the helical toothing 23 is provided, the sleeve 17a being arranged to be axially displaceable and rotatable on the drive shaft element 5a. Similarly, although not shown, where appropriate the outer ring 18 may have a sleeve coupled therewith and having helical teeth for cooperation with helical teeth of the displacement ring.

I claim:
1. A dental handpiece comprising a holding sleeve (1);
a head sleeve (2) connected to said holding sleeve (1) and adapted to mount rotatably a dental tool (9), said head sleeve (2) having its lognitudinal axis inclined relative to the longitudinal axis of the holding sleeve (1);
a connecting zone providing an interconnection between said holding sleeve (1) and said head sleeve (2);
a two-drive shaft housed within the handpiece, a first part (5b) of the shaft (5) being arranged within the holding sleeve (1) and a second part (5a) of the shaft (5) being arranged within the head sleeve (2);
a transmission (7) providing a drive connection between said first and second parts (5b, 5a) of the shaft (5), said transmission (7) being housed within said connecting zone;
wherein the transmission comprises a ball-type planetary transmission (7) including an inner ring (17), an outer ring (18), balls (16) frictionally engageable between said rings; a cage engaging said balls (16);

one of said parts (5b or 5a) of the drive shaft (5) is coupled drivingly with said cage, one of said rings (17 or 18) is non-rotatably mounted in said connecting zone, and a coupling element (19) is secured to the other of said parts (5a or 5b, respectively) of the shaft (5); the other of said rings (18 or 17, respectively) is coupled with said other parts (5a or 5b, respectively) of the shaft (5) for rotation therewith, said other ring (18 or 17, respectively) having a drive transmitting connection with said coupling element (19) and being axially displaceable relative to said other part (5a or 5b, respectively) of the shaft (5) in order to adjust the frictional engagement of said balls (16) between said inner and outer rings (17 and 18) thereby to alter the value of torque transmissible by the shaft (5);

and wherein said drive transmitting connection comprises interengaging helical teeth (22, 23) provided on said coupling element (19) and on said other ring (18 or 17, respectively).

2. A dental handpiece comprising a holding sleeve;

a head sleeve connected to said holding sleeve and adapted rotatably to mount a dental instrument;

a connecting zone providing an interconnection between said holding sleeve and said head sleeve;

a two-part drive shaft housed within the handpiece, a first part of the shaft being arranged within the holding sleeve and a second part of the shaft being arranged within the head sleeve;

and a ball-type planetary transmission housed within the said connecting zone and providing a drive connection between said first and second parts, the ball-type planetary transmission comprising an inner ring, an outer ring, balls frictionally engageable between said rings, and a cage engaging said balls;

wherein one of said parts of the drive shaft is coupled drivingly with said cage;

one of said rings is non-rotatably mounted in said connecting zone;

a coupling element is secured to the other of said parts of the shaft;

and the other of said rings is coupled with said other part of the shaft for rotation therewith, said other ring haveing a drive transmitting connection with said coupling element and being axially displaceable relative to said other part of the shaft in order to adjust the frictional engagement of said balls between said inner and outer rings thereby to alter the value of torque transmissible by the shaft;

and wherein said drive transmitting connection comprises interengaging helical teeth provided on said coupling element and on said other ring.

3. A handpiece according to claim 2, wherein said head sleeve is connected to said holding sleeve with its longitudinal axis inclined relative to the longitudinal axis of the holding sleeve.

4. A handpiece according to claim 2, wherein said head sleeve is connected to said holding sleeve with its longitudinal axis substantially parallel to the longitudinal axis of the holding sleeve.

5. A handpiece according to claim 2, wherein said coupling element is secured to said second part of the shaft.

6. A handpiece according to claim 2, wherein said inner ring is axially displaceable relative to said second part of the shaft, and is rotatable with said second part via the helical teeth of said drive transmitting connection, said first part of the shaft being coupled with said cage.

7. A handpiece according to claim 2, wherein said helical teeth are uniformally distributed about the periphery of said coupling element and said other ring.

8. A handpiece according to claim 2, wherein a sleeve is secured to said other ring and extends towards said coupling element, said sleeve being provided with said helical teeth of said other ring, and said sleeve being mounted for axial and rotational movement on said second part of the shaft.

9. A handpiece according to claim 2, wherein the tooth profiles of said helical teeth are straight.

10. A handpiece according to claim 2, wherein the tooth profiles of said helical teeth are curved.

* * * * *